(12) United States Patent
Park et al.

(10) Patent No.: US 7,203,627 B2
(45) Date of Patent: Apr. 10, 2007

(54) METHOD FOR PROCESSING MISSING VALUES IN MEASURED DATA

(75) Inventors: Kyunghee Park, Seoul (KR); Yunsun Nam, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/060,271

(22) Filed: Feb. 17, 2005

(65) Prior Publication Data

US 2005/0216202 A1 Sep. 29, 2005

(30) Foreign Application Priority Data

Feb. 19, 2004 (KR) ............ 10-2004-0011001

(51) Int. Cl.
*G06F 13/00* (2006.01)

(52) U.S. Cl. .............. 702/194; 702/179; 702/189; 702/190

(58) Field of Classification Search ............... 702/119, 702/120, 128, 179, 183, 199, 189, 190, 194; 382/271; 700/19; 707/21; 435/6
See application file for complete search history.

(56) References Cited

U.S. PATENT DOCUMENTS

| 5,025,404 | A | * | 6/1991 | Janssen et al. | 708/290 |
| 6,519,576 | B1 | * | 2/2003 | Freeman | 706/21 |
| 6,980,691 | B2 | * | 12/2005 | Nesterov et al. | 382/165 |
| 2005/0089906 | A1 | * | 4/2005 | Furuta et al. | 435/6 |

* cited by examiner

*Primary Examiner*—Marc S. Hoff
*Assistant Examiner*—Felix Suarez
(74) *Attorney, Agent, or Firm*—Cantor Colburn LLP

(57) ABSTRACT

A method for processing missing values in measured data is provided. The method includes assigning weights to measured objects or measured items, according to a priority of the measured objects or measured items; selecting a set of the measured objects and measured items including the missing values having the smallest sum of the weights among a plurality of sets of the measured objects and measured items including the missing values; and removing the measured objects and measured items included in the selected set from the measured data.

11 Claims, 5 Drawing Sheets

|  | SNP 1 (0.5) | SNP 2 (1) | SNP 3 (1) | SNP 4 (1) | SNP 5 (2) | SNP 6 (2) |
|---|---|---|---|---|---|---|
| SAMPLE 1 (1) | * | * |  |  |  |  |
| SAMPLE 2 (1) |  |  |  | * |  |  |
| SAMPLE 3 (1) | * |  | * |  |  |  |
| SAMPLE 4 (1) |  | * |  |  |  |  |
| SAMPLE 5 (1) | * |  |  |  | * |  |
| SAMPLE 6 (1) |  |  |  |  |  |  |

\* : MISSING VALUE    ( ) : WEIGHT

FIG. 3A

|  | SNP 1 (0.5) | SNP 2 (1) | SNP 3 (1) | SNP 4 (1) | SNP 5 (2) | SNP 6 (2) |
|---|---|---|---|---|---|---|
| SAMPLE 1 (1) | * | * |  |  |  |  |
| SAMPLE 2 (1) |  |  |  | * |  |  |
| SAMPLE 3 (1) | * |  | * |  |  |  |
| SAMPLE 4 (1) |  | * |  |  |  |  |
| SAMPLE 5 (1) | * |  |  |  | * |  |
| SAMPLE 6 (1) |  |  |  |  |  |  |

FIG. 3B

|  | SNP 1 (0.5) | SNP 2 (1) | SNP 3 (1) | SNP 4 (1) | SNP 5 (2) | SNP 6 (2) |
|---|---|---|---|---|---|---|
| SAMPLE 1 (1) | * | * |  |  |  |  |
| SAMPLE 2 (1) |  |  |  | * |  |  |
| SAMPLE 3 (1) | * |  | * |  |  |  |
| SAMPLE 4 (1) |  | * |  |  |  |  |
| SAMPLE 5 (1) | * |  |  |  | * |  |
| SAMPLE 6 (1) |  |  |  |  |  |  |

FIG. 5

| SAMPLE | SNP 1 | SNP 2 | SNP 3 | SNP 4 | SNP 5 | SNP 6 | SNP 7 | SNP 8 | SNP 9 | SNP 10 |
|---|---|---|---|---|---|---|---|---|---|---|
| 1 | 0 | | 1 | 2 | 1 | 1 | 1 | 2 | 1 | 1 |
| 2 | 1 | 2 | 2 | 2 | 0 | 1 | 1 | 1 | 1 | 2 |
| 3 | 0 | | 2 | 2 | 1 | 1 | 2 | 0 | 1 | 0 |
| 4 | 2 | 0 | | 2 | | 1 | 2 | 2 | 1 | |
| 5 | | 2 | 1 | 2 | 1 | 1 | 1 | 1 | 1 | 0 |
| 6 | | 1 | 0 | 2 | 1 | 1 | 1 | 0 | 1 | 2 |
| 7 | 1 | | 1 | 2 | 1 | 2 | 1 | | 1 | 1 |
| 8 | 2 | 2 | 1 | 2 | | 1 | 2 | 1 | 1 | 1 |
| 9 | | 1 | 1 | 2 | 1 | 1 | 2 | 2 | | 0 |
| 10 | 1 | 2 | 2 | 2 | 2 | | 0 | 1 | 1 | 0 |
| 11 | 1 | | 2 | 2 | 0 | 1 | 1 | 2 | 1 | 1 |
| 12 | | 1 | | 1 | | 1 | 2 | 2 | 1 | 1 |
| 13 | | 2 | 1 | | 2 | | 2 | 1 | 1 | 0 |
| 14 | | | 1 | 2 | 0 | 1 | 2 | 0 | 1 | 0 |
| 15 | | | 1 | 1 | 1 | 1 | 2 | 2 | 1 | 2 |
| 16 | 2 | | | 2 | 1 | 1 | 0 | 1 | 1 | 2 |
| 17 | 0 | 1 | 1 | 2 | 1 | 1 | 1 | | 1 | 0 |
| 18 | 0 | | 2 | 2 | 1 | 1 | 1 | 1 | | 2 |
| 19 | 2 | | 2 | | | 1 | 2 | 1 | 1 | 0 |
| 20 | 0 | 2 | 1 | | 2 | 1 | 1 | 1 | 1 | 1 |

| SNP | 1 | 2 | 3 | 4 | 5 | 6 | 7 | 8 | 9 | 10 |
|---|---|---|---|---|---|---|---|---|---|---|
| WEIGHT | 3 | 3 | 3 | 2 | 2 | 2 | 0.5 | 0.5 | 0.5 | 0.5 |

US 7,203,627 B2

METHOD FOR PROCESSING MISSING VALUES IN MEASURED DATA

BACKGROUND OF THE INVENTION

This application claims the priority of Korean Patent Application No. 10-2004-0011001, filed on Feb. 19, 2004, in the Korean Intellectual Property Office, the disclosure of which is incorporated herein in its entirety by reference.

1. Field of the Invention

The present invention relates to a method for processing missing values in measured data, and more particularly, to a method for analyzing genotypic information having missing values.

2. Description of the Related Art

High-throughput genotyping technology has enabled generation of a vast amount of genotypic information with a large number of samples at a time. This genotyping technology has been used to analyze a nucleotide sequence of a target sample or single nucleotide polymorphism (SNP) information of a target gene. The high-throughput genotyping technology has been also used to search disease related genes or draw genetic maps based on the SNP information. Genotypic information is expressed in a form of a matrix where rows denote samples and columns denote genes or SNP positions.

Because high-throughput genotyping is performed on a large scale, genotyping error including missing values, for example, may exist in the genotypic information. Accordingly, when genetic experiments, for example, are performed on a large scale with missing values frequently occurring, a method for processing missing values while minimizing loss in the remaining measured data is needed.

SUMMARY OF THE INVENTION

The present invention provides a method for analyzing genotypic information capable of minimizing the loss of generated genotypic information while improving reliability of the genotyping.

According to an aspect of the present invention, a method for processing missing values in measured data including a plurality of missing values. The method comprises assigning weights to measured objects or measured items, according to a priority of the measured objects or measured items; selecting a set of the measured objects and measured items including the missing values having the smallest sum of the weights among a plurality of sets of the measured objects and measured items including the missing values; and removing the measured objects and measured items included in the selected set from the measured data.

According to another aspect of the present invention, a method for processing missing values in genetic data. The method comprises assigning weights to samples or single nucleotide polymorphism positions according to a priority of the samples or single nucleotide polymorphism positions; selecting a set of the samples and single nucleotide polymorphism positions including the missing values having the smallest sum of weights among sets of the samples and single nucleotide polymorphism positions including the missing values; and removing the samples and single nucleotide polymorphism positions included in the selected set from the genetic data.

According to further aspect of the present invention, a computer readable recording medium has embodied thereon a code for executing a method of processing missing values, such as analyzing genotypic information having missing values.

BRIEF DESCRIPTION OF THE DRAWINGS

The above and other features and advantages of the present invention will become more apparent by describing in detail exemplary embodiments thereof with reference to the attached drawings in which:

FIGS. 3A and 3B show exemplary sets of samples and SNP positions having the missing values shown in FIG. 2;

FIG. 5 illustrates genotypic information having missing values, which are occurred with respect to twenty samples (SAMPLE 1 to 20) and SNP positions (SNP1 to 10);

DETAILED DESCRIPTION OF THE INVENTION

The present invention will now be described more fully with reference to the accompanying drawings, in which exemplary embodiments of the invention are shown.

Figures 1, 2:
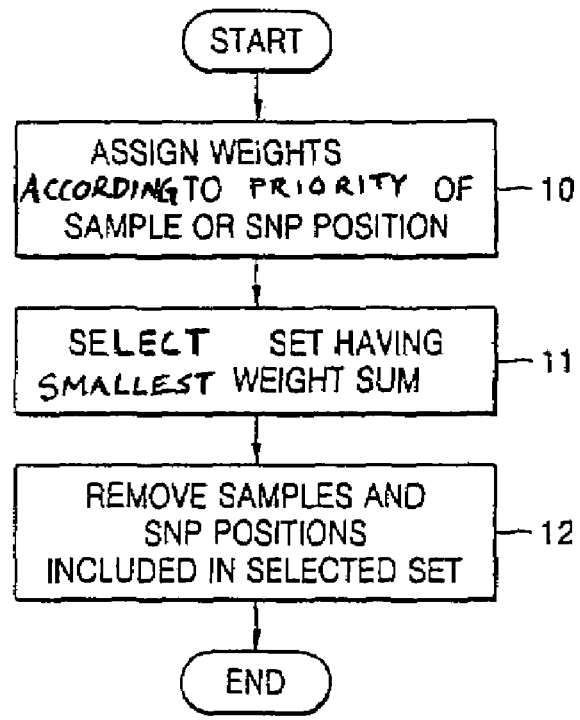
FIG. 1 is a flowchart of a method for analyzing genotypic information having missing values, according to an exemplary embodiment of the present invention.
FIG. 2 illustrates exemplary genotypic information having missing values, which have occurred with respect to six samples (SAMPLE 1 to 6) and six single nucleotide polymorphism (SNP) positions (SNP 1 to 6)

FIG. 1 is a flowchart of a method for processing missing values, such as analyzing genotypic information having missing values, according to an exemplary embodiment of the present invention. Referring to FIG. 1, a different weight is assigned to a measured object or a measured item according to a priority of the measured object or item (step 10). The measured object, for example, includes a measured sample, and the measured item includes a single nucleotide polymorphism (SNP) position. The priority of a measured sample depends on what is a subject matter of the genotyping. The priority of the SNP position also depends on how much the SNP position is related to a target disease.

FIG. 2 illustrates genotypic information having missing values, which have occurred with respect to the samples and SNP positions. In the table of FIG. 2, the columns indicate six SNP positions (SNP 1 to SNP 6), and the rows indicates six samples (SAMPLE 1 to SAMPLE 6). An identical weight is assigned to the samples (SAMPLE 1 to SAMPLE 6), and different weights are assigned to SNP positions (SNP1 to SNP6). The numbers in parentheses represent the weights assigned to the samples and SNP positions, respectively, and the symbol '*' indicates that genetic data of a sample is missing at a SNP position.

FIGS. 3A and 3B show exemplary sets of samples and SNP positions having the missing values shown in FIG. 2. In FIG. 3A, the sets consist of samples (SAMPLE 1, 4, and 5) and SNP positions (SNP 1, 3, and 4), and a sum of weights of corresponding rows and columns is 5.5. In FIG. 3B, the sets consist of samples (SAMPLE 3 and 5) and SNP positions (SNP 1, 2, and 4), and a sum of weights of corresponding rows and columns is 4.5. The samples and SNP positions of the sets defined in FIGS. 3A and 3B can be removed from a whole of genotypic information in order to increase reliability of the genotyping results. In the exemplary embodiment, the sets shown in FIG. 3B having a smaller sum of weights than that of the sets shown in FIG. 3A is selected. Therefore, a set having the smallest sum of weights is selected from sets of the samples and SNP positions having the missing values (step 11). When the set having the smallest sum of weights is selected, the samples and SNP positions included in the selected set is removed from the genotypic information (step 12).

Here, the step for selecting a set of samples and SNP positions having the smallest sum of weights will now be explained in more detail. When the number of samples or SNP positions is small as in FIGS. 3A and 3B, an analyzer is used to manually calculate the sum of weights of each set having missing values. However, if the number of samples or SNP positions is too big for the analyzer to manually calculate the sum of weights of each set, a computer is used to process the selecting step. According to the exemplary embodiment, a bipartite graph and a method for solving a weighted vertex cover problem may be used in the selecting process.

Figure 4:
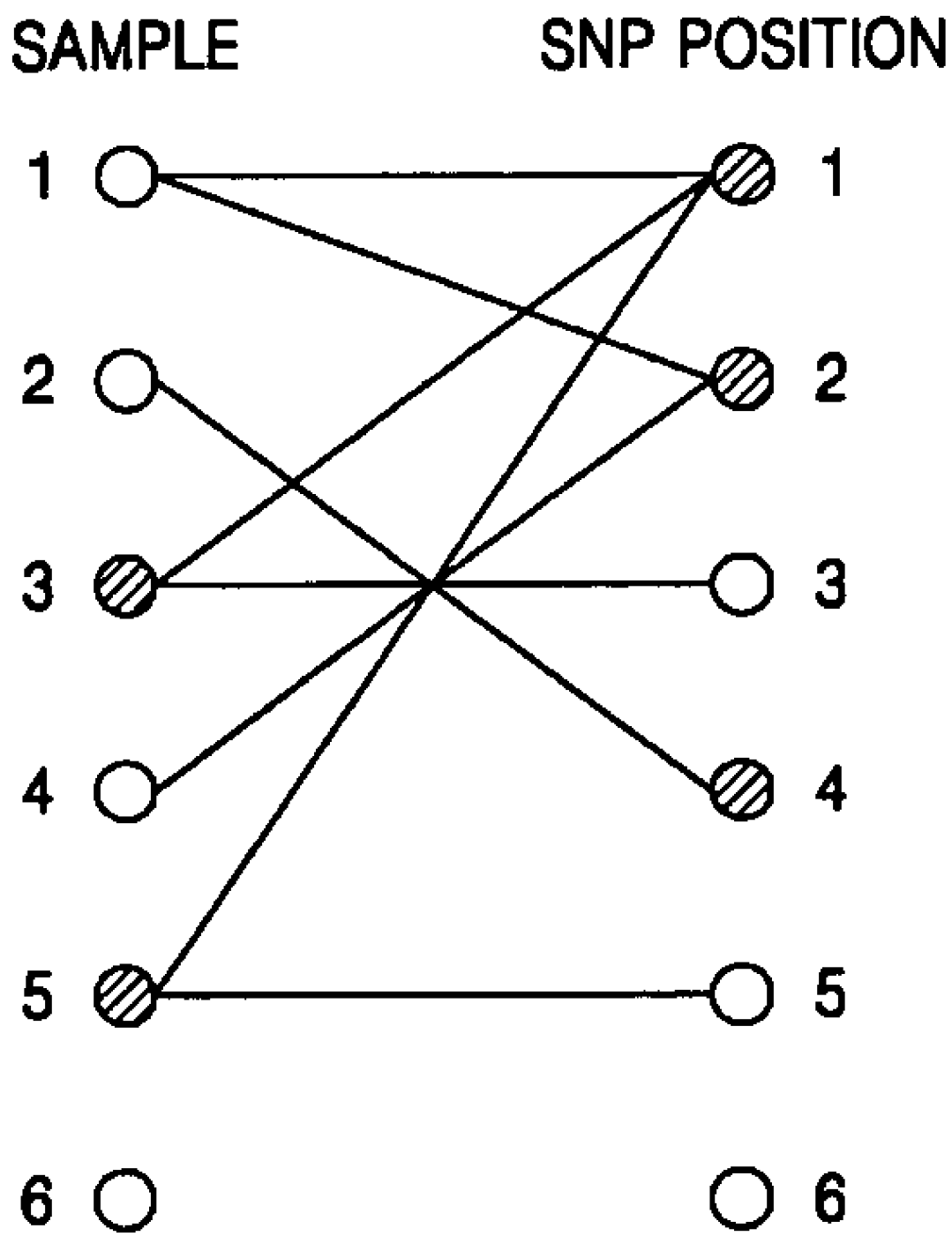
FIG. 4 is a bipartite graph of the missing values shown in FIG. 2.

FIG. 4 illustrates a bipartite graph of missing values shown in FIG. 2. Samples (SAMPLE 1 to 6) are placed as vertices of one side of a bipartite graph and SNP positions (SNP 1 to 6) are placed as vertices of the other side of the bipartite graph. A weight of a SNP position or sample is assigned to a corresponding vertex. Then, the vertices of the samples are connected to the vertices of the SNP positions by edges, respectively, at which the missing values occur. For example, when a missing value occurs at SNP position (SNP 1) in a sample (SAMPLE 3), the vertices of the sample (SAMPLE 3) and SNP position (SNP 1) are connected by an edge.

The bipartite graph to which weights are thus assigned is converted to a weighted vertex cover problem. A vertex cover is a partial set of vertex set covering all edges in the graph. By using the weighted vertex cover problem, a vertex cover having the smallest sum of weights is obtained. Therefore, the SNP positions or samples, corresponding to the vertices of the set obtained by using the solution of the weighted vertex cover problem, are removed from the genotypic information. The vertices marked by solid lines, in FIG. 4, correspond to the samples and SNP positions to be removed from genotypic information.

The vertex cover problem can be solved in various methods, and Hungarian method is a leading one. The Hungarian method is disclosed in a book by Christos H. Papadimitiou and Kenneth Steiglitz, "Combinatorial optimization: Algorithms and complexity", 1982, Prentice-Hall.

FIG. 5 illustrates genotypic information having missing values, which occur with respect to samples (SAMPLE 1 to 20) and SNP positions (SNP 1 to 10). The genotypic information has thirty-three missing values, which are each indicated as an empty cell in the table. The values "0", "1", and "2" respectively indicate the types of nucleotide sequences, which can be obtained from two chromosomes in one sample at each SNP position. For example, the value "0" denotes AA, the value "1" denotes AT, and the value "2" denotes TT. A weight "1" is assigned to each sample, and different weights are assigned to the SNP positions depending on the priority of the SNP positions, as shown in FIG. 6.

Figures 6, 7:
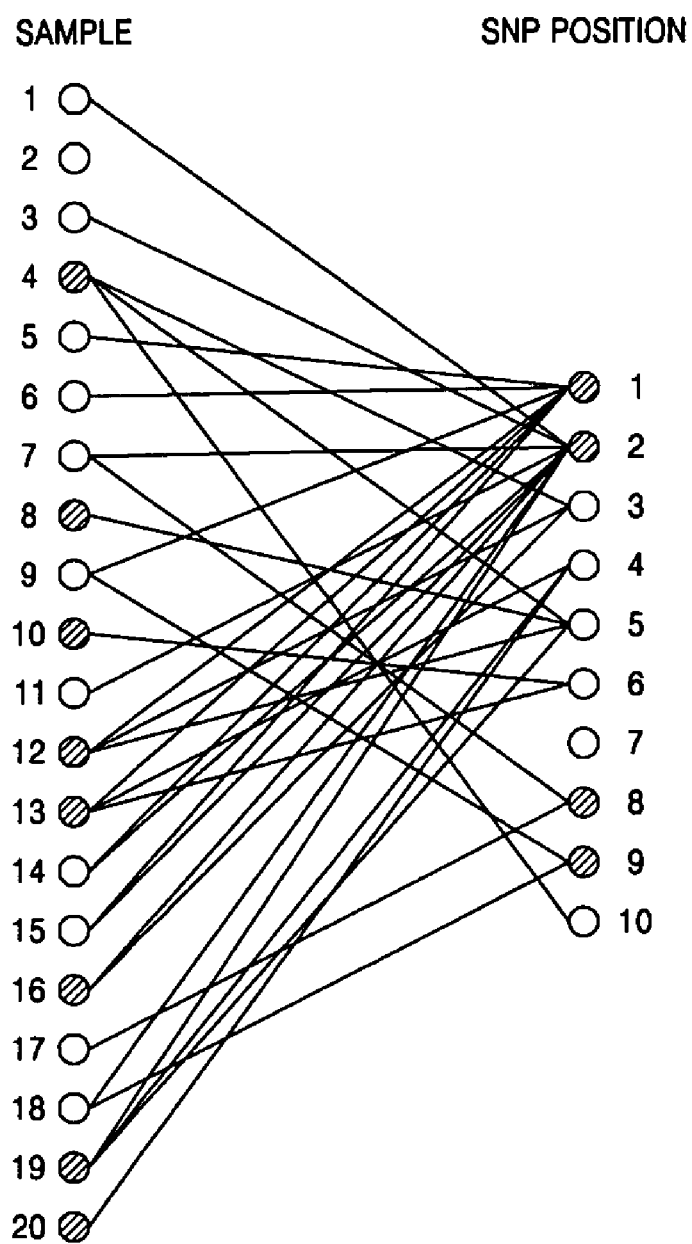
FIG. 6 illustrates examples of weights assigned to the SNP positions shown in FIG. 5.
FIG. 7 is a bipartite graph of the missing values shown in FIG. 5.

FIG. 7 is a bipartite graph of missing values shown in FIG. 5. The bipartite graph and weights are converted into a weighted vertex cover problem to select a set of the samples and SNP positions having the smallest sum of weights. As shown in FIG. 7, the set consisting of SNP positions (SNP 1, 2, 8, and 9) and samples (SAMPLE 4, 8, 10, 12, 13, 16, 19, and 20) has the sum of weights of 13, and is determined to have the smallest sum among sets of SNP positions and samples including missing values. Thus, the set consisting of SNP positions (SNP 1, 2, 8, and 9) and samples (SAMPLE 4, 8, 10, 12, 13, 16, 19, and 20) is selected, and the SNP positions (SNP 1, 2, 8, and 9) and samples (SAMPLE 4, 8, 10, 12, 13, 16, 19, and 20) are removed from the genotypic information shown in FIG. 5.

The method for processing missing values in genetic data, such as analyzing genotypic information having missing values, for example, according to the present invention can be embodied as computer readable codes on a computer readable recording medium. The computer readable recording medium includes any data storage device that can store data and read the data through a computer system.

Examples of the computer readable recording medium include read-only memory (ROM), random-access memory (RAM), CD-ROMs, magnetic tapes, floppy disks, optical data storage devices, and carrier waves such as data transmission through the Internet. The computer readable recording medium can also be performed over a network coupled to computer systems. The computer readable code is distributed via the network, and stored and executed at the computer systems coupled to the network.

Since the method for analyzing genotypic information having missing values, according to the present invention, assigns different weights to samples or SNP positions based on the priority of the samples or SNP positions, selects a set of samples and SNP positions having the smallest sum of weights, and removes the samples and SNP positions included in the selected set from the genotypic information, the method can prevent the genotypic information from having missing values, as well as minimizing the loss of important generic data.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A method for processing missing values in measured data including a plurality of missing values, the method comprising:

assigning weights to a plurality of measured objects or a plurality of measured items, according to a priority of the measured objects or measured items;

selecting a set of the measured objects and measured items including the missing values having the smallest sum of the weights among a plurality of acts of the measured objects and measured items including the missing values; and removing the measured objects and measured items included in the selected set from the measured data, wherein each measured item of plurality of measured items is assigned to each measured object.

2. The method of claim 1, wherein selecting the set having the smallest sum of the weights comprises:

generating a bipartite graph by placing the measured objects as vertices of one side of the bipartite graph, and the measured items as vertices of the other side of the bipartite, and connecting each of the vertices of the measured objects and each of the vertices of the measured items by an edge, at which each missing value occur;

assigning the weights assigned to the measured objects or measured items to corresponding vertices of the measured objects or measured items, respectively; and selecting a vertex cover having the smallest sum of weights, among vertex covers.

3. The method of claim 1, wherein selecting a set having the smallest sum of weights comprises:

generating a bipartite graph by placing the measured objects as vertices of one side of the bipartite graph, and the measured items as vertices of the other side of the bipartite graph, and connecting each of the vertices of the measured objects and each of the vertices of the measured items by an edge; at which each missing value occurs;

converting the bipartite graph into a weighted vertex cover problem to solve the weighted vertex cover problem; and selecting a vertex cover having the smallest sum of weights.

4. The method of claim 2, wherein the weighted vertex cover problem is solved in a Hungarian method.

5. The method of claim 1, wherein the measured objects include measured samples, and the measured items include SNP positions.

6. A method for processing missing values in genetic data, the method comprising:

assigning weights to samples or single nucleotide polymorphism positions according to a priority of the samples or single nucleotide polymorphism positions;

selecting a set of the samples and single nucleotide polymorphism positions including the missing values having the smallest sum of weights among sets of the samples and single nucleotide polymorphism positions including the missing values; and removing the samples and single nucleotide polymorphism positions included in the selected set from the genetic data.

7. The method of claim 6, wherein the priority of the single nucleotide polymorphism positions depends on a relation between a target disease and the single nucleotide polymorphism positions.

8. The method of claim 6, wherein selecting a set having the smallest sum of the weights comprises:

generating a bipartite graph by placing the samples as vertices of one side of the bipartite graph, and the single nucleotide polymorphism positions as vertices of the other side of the bipartite graph, and connecting each of the vertices of the samples and each of the vertices of the single nucleotide polymorphism positions by an edge, at which each missing value occurs;

assigning the weights assigned to the samples or single nucleotide polymorphism positions to corresponding vertices of the samples or single nucleotide polymorphism positions, respectively; and selecting a vertex cover having the smallest sum of weights among vertex covers.

9. The method of claim 6, wherein selecting the set having the smallest sum of the weights comprises:

generating a bipartite graph by placing the samples as vertices of one side of the bipartite graph, and the single nucleotide polymorphism positions as vertices of the other side of the bipartite graph;

connecting each of the vertices of the samples and each of the vertices of the single nucleotide polymorphism positions by an edge, at which each missing value occurs;

converting the bipartite graph into a weighted vertex cover problem to solve the weighted vertex cover problem; and selecting a vertex cover having the smallest sum of weights.

10. A computer readable recording medium having embodied thereon a code for executing a method of claim 1.

11. A computer readable recording medium having embodied thereon a code for executing a method of claim 6.

* * * * *